(12) United States Patent
Reicher (10) Patent No.: US 10,304,564 B1
(45) Date of Patent: May 28, 2019

(54) METHODS AND SYSTEMS FOR DISPLAYING AN IMAGE

(71) Applicant: INTERNATIONAL BUSINESS MACHINES CORPORATION, Armonk, NY (US)

(72) Inventor: Murray A. Reicher, Rancho Santa Fe, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/840,768

(22) Filed: Dec. 13, 2017

(51) Int. Cl.
| G06F 17/00 | (2019.01) |
| G16H 30/20 | (2018.01) |
| G16H 10/60 | (2018.01) |
| G06F 17/21 | (2006.01) |
| G06K 9/62 | (2006.01) |

(52) U.S. Cl.
CPC ........... G16H 30/20 (2018.01); G06F 17/212 (2013.01); G06K 9/628 (2013.01); G16H 10/60 (2018.01)

(58) Field of Classification Search
CPC . G06F 17/30247; G06F 19/321; G06F 17/212
See application file for complete search history.

(56) References Cited

U.S. PATENT DOCUMENTS

| 7,593,967 | B2* | 9/2009 | Harnsberger | ........... G06F 17/24 |
| 7,783,094 | B2* | 8/2010 | Collins | .................... A61B 6/00 |
| | | | | 382/128 |
| 8,165,368 | B2 | 4/2012 | Vijaykalyan et al. | |
| 8,391,574 | B2* | 3/2013 | Collins | .................... A61B 8/08 |
| | | | | 382/128 |
| 8,923,580 | B2 | 12/2014 | Dekel et al. | |
| 9,152,759 | B2 | 10/2015 | Novatzky et al. | |

(Continued)

FOREIGN PATENT DOCUMENTS

EP 2172860 A1 4/2010

OTHER PUBLICATIONS

Wang et al., "Intelligent Tools for a Productive Radiologist Workflow: How Machine Learning Enriches Hanging Protocols", CPACS Radiology Productivity Results Summary Final, 2013, 8 pages, General Electric Company.

(Continued)

*Primary Examiner* — Laurie A Ries
(74) *Attorney, Agent, or Firm* — Michael Best & Friedrich LLP (57) ABSTRACT

Methods and systems for displaying a medical image captured as part of a medical imaging procedure. One system includes an electronic processor configured to receive a plurality of images from an image database, the plurality of images included in a medical exam associated with the procedure. The electronic processor is also configured to automatically determine a classification for each of the plurality of images using a classification model analyzing content of each of the plurality of images, the classification including one of a textual image and an anatomical image. The electronic processor is also configured to determine a set of rules displaying the plurality of images and display a subset of the plurality of images based on the classification determined for each of the plurality of images and the set of rules.

20 Claims, 3 Drawing Sheets

(56) References Cited

U.S. PATENT DOCUMENTS

| | | | |
|---|---|---|---|
| 9,152,760 B2 | 10/2015 | Sherman et al. | |
| 9,245,337 B2* | 1/2016 | Schmidt | G06K 9/6253 |
| 2007/0014454 A1* | 1/2007 | Sawyer | A61N 5/1049 |
| | | | 382/128 |
| 2009/0129643 A1* | 5/2009 | Natanzon | G06F 19/321 |
| | | | 382/128 |
| 2011/0093293 A1* | 4/2011 | G. N. | G06Q 10/06 |
| | | | 705/3 |
| 2014/0143710 A1* | 5/2014 | Zhao | G06F 19/321 |
| | | | 715/781 |
| 2015/0161169 A1* | 6/2015 | Fry | G06F 17/30265 |
| | | | 707/738 |
| 2015/0254403 A1* | 9/2015 | LaPerna | G06F 19/322 |
| | | | 705/3 |
| 2016/0063699 A1* | 3/2016 | Gustafson | G06F 19/321 |
| | | | 715/738 |
| 2016/0210427 A1* | 7/2016 | Mynhier | G06F 19/345 |
| 2016/0239564 A1* | 8/2016 | Sohma | G06F 17/30713 |
| 2016/0335403 A1 | 11/2016 | Mabotuwana et al. | |
| 2017/0154167 A1 | 6/2017 | Ovtchinnikov | |
| 2018/0338741 A1* | 11/2018 | Lyman | G06F 19/321 |

OTHER PUBLICATIONS

"PACS—Alive and Kicking", Visus View Catalog, Jul. 2017, No. 7, 32 pages, Visus.

* cited by examiner

METHODS AND SYSTEMS FOR DISPLAYING AN IMAGE

FIELD

Embodiments described herein relate to methods and systems for displaying an image, and more particularly, to displaying an image based on a classification of the image using image analytics.

SUMMARY

Physicians and other medical professionals typically use a commercial picture archive and communication system ("PACS") when reviewing medical images (for example, medical image studies or exams). PACS provide an automated presentation of medical images in accordance with a "hanging" protocol. A hanging protocol is a rule-based protocol for the automated presentation of medical images. The hanging protocol is generally based on a reviewer's preferences, such as a reviewer's preferences per modality, exam type, exam group (for example, a collection of exam types), and the like. For example, a hanging protocol determines which and how many comparison exams are selected, a number of medical images presented from each exam, how the medical images are arranged, and the like. Additionally, PACS may allow a reviewer to "toggle" or "shuffle" between medical images to improve the speed and accuracy of image interpretation.

Whether using image toggling, image shuffling, or another presentation arrangement, PACS typically depend on information (for example, metadata) in associated meta-files, such as digital imaging and communications in medicine ("DICOM") information, to characterize images and invoke a set of rules based on image characteristics. Unfortunately, such meta-files may not contain accurate or sufficient information to differentiate between various classifications of medical images.

Exams (for example, a collection of medical images) often include a variety of image types, such as anatomical images and textual images. An anatomical image may refer to a medical image that represents anatomy. A textual image may refer to a medical image that shows text or other data. A textual image may include, for example, scanned or pictured forms, such as a radiation dose report, or even native DICOM images. For example, an exam might include a posterior anterior ("PA") chest radiograph, a lateral chest radiograph, and other formatted images of various text files, such as referral forms, technologist worksheets, medical record request forms, billing forms, screening forms, and the like. The inclusion of textual images within the exam interferes with the application of hanging protocols, and ultimately, with the display of the exam to a reviewer.

To solve these and other problems, embodiments described herein provide methods and systems for displaying a medical image based on a classification of the medical image. The methods and systems process an exam to determine a classification of each medical image included in the exam. The methods and systems display the medical images to a user based on the classifications associated with each medical image. Alternatively or in addition, the methods and systems may display the medical images based on a set of rules (for example, a hanging protocol).

For example, one embodiment provides a system for displaying a medical image captured as part of a medical imaging procedure. The system includes an electronic processor configured to receive a plurality of images from an image database, the plurality of images included in a medical exam associated with the procedure. The electronic processor is also configured to automatically determine a classification for each of the plurality of images using a classification model analyzing content of each of the plurality of images, the classification including one of a textual image and an anatomical image. The electronic processor is also configured to determine a set of rules displaying the plurality of images and display a subset of the plurality of images based on the classification determined for each of the plurality of images and the set of rules.

Another embodiment provides a method for displaying a medical image captured as part of a medical imaging procedure. The method includes receiving, with an electronic processor, the plurality of medical images from a medical image database. The method also includes determining, with the electronic processor, a classification of each of the plurality of medical images using a classification model, wherein the classification of each of the plurality of medical images includes one of a textual image and an anatomical image. The method also includes determining, with the electronic processor, a set of rules for the plurality of medical images. The method also includes displaying, with the electronic processor, a first display of at least a subset of the plurality of medical images to a user via a display device based on the classification of each of the plurality of medical images and the set of rules. The method also includes receiving, with the electronic processor, a user interaction with at least one of the plurality of medical images and displaying, with the electronic processor, a second display of the medical images based on the user interaction.

Another embodiment provides a non-transitory, computer-readable medium storing instructions that, when executed by an electronic processor, perform a set of functions. The set of functions includes receiving a first medical image from a medical image database in response to a request form a user for images included in a medical exam. The set of functions also includes automatically determining a first classification of the first medical image using a classification model, the classification model classifying an image as a textual image or an anatomical image. The set of functions also includes automatically determining whether to display the first medical image to a user based on the first classification. The set of functions also includes receiving a second medical image from the medical image database in response to the request and automatically determining a second classification of the second medical image using the classification model. The set of functions also includes automatically determining whether to display the second medical image to the user based on the second classification.

Other aspects of the embodiments described herein will become apparent by consideration of the detailed description and accompanying drawings.

Other aspects of the embodiments described herein will become apparent by consideration of the detailed description.

DETAILED DESCRIPTION

Before embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Also, electronic communications and notifications may be performed using any known means including direct connections, wireless connections, etc.

A plurality of hardware and software based devices, as well as a plurality of different structural components may be utilized to implement the embodiments described herein. In addition, embodiments described herein may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the embodiments described herein may be implemented in software (for example, stored on non-transitory computer-readable medium) executable by one or more processors. As such, it should be noted that a plurality of hardware and software based devices, as well as a plurality of different structural components, may be utilized to implement the embodiments described herein. For example, "mobile device," "computing device," and "server" as described in the specification may include one or more electronic processors, one or more memory modules including non-transitory computer-readable medium, one or more input/output interfaces, and various connections (for example, a system bus) connecting the components.

As described above, exams (for example, a collection of medical images) often include a variety of image classifications or image types, such as anatomical images and textual images. An anatomical image may refer to a medical image that represents anatomy, such as a lateral chest radiograph. A textual image may refer to a medical image that shows text or other data. A textual image may include, for example, scanned or pictured forms, such as a radiation dose report, or even native DICOM images. For example, an exam might include a posterior anterior ("PA") chest radiograph, a lateral chest radiograph, and other formatted images of various text files, such as referral forms, technologist worksheets, medical record request forms, billing forms, screening forms, and the like. The variety of image classifications or types included in an exam interferes with the application of hanging protocols, and ultimately, with the display of the exam to a reviewer.

Figure 1:
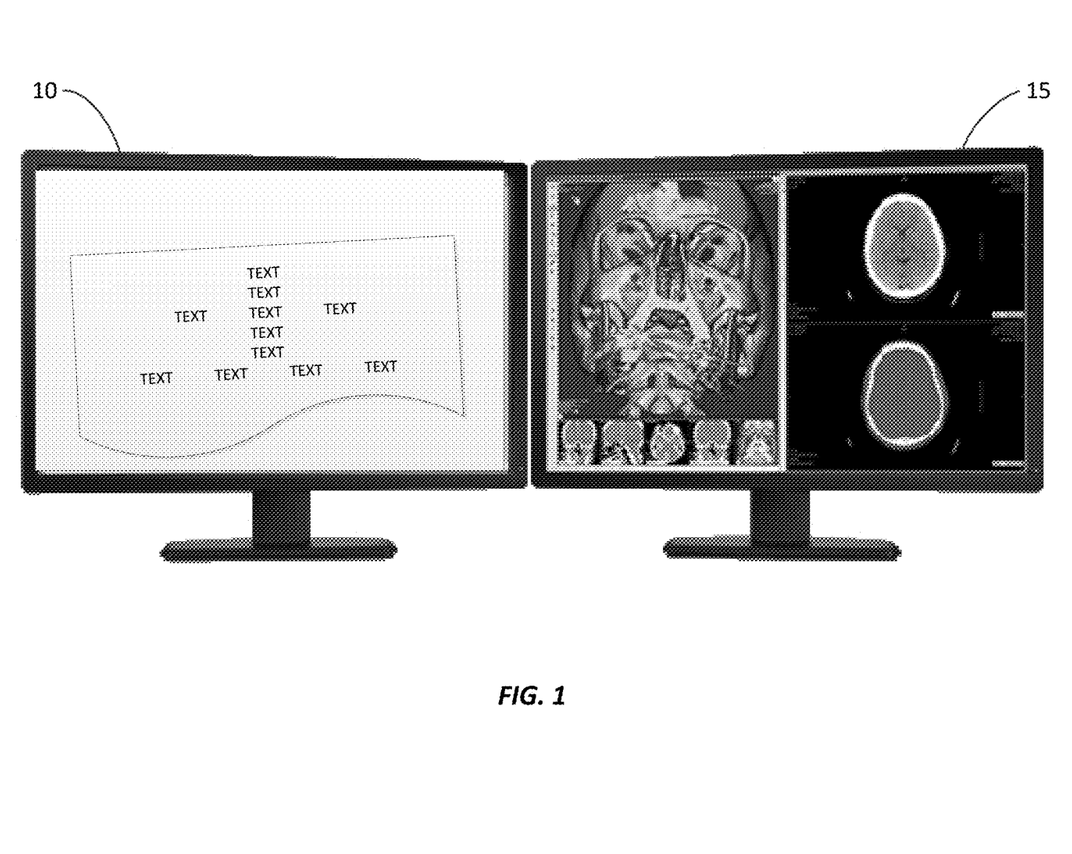
FIG. 1 illustrates a set of display devices displaying a medical exam according to some embodiments.

For example, FIG. 1 illustrates a first display device 10 and a second display device 15 illustrating a medical exam. As noted above, the medical exam may include a plurality of medical images. The medical images included in the medical exam may include a variety of image classifications or types, including anatomical images and textual images. For example, as illustrated in FIG. 1, the first display device 10 displays a textual image, such as a scanned document, and the second display device 15 discloses a plurality of anatomical images. While a reviewer toggles or shuffles through the medical images included in the exam, the reviewer may be interrupted with one or more textual images that are irrelevant to the objective of the reviewer. For example, a reviewing physical may shuffle through medical images to determine a diagnosis of a patient. However, as the reviewing physician shuffles through various anatomical images, a billing form (for example, a textual image) may be displayed to the reviewing physician. Accordingly, the reviewing physician is interrupted by a billing form that is irrelevant to the diagnosis of the patient. Also, the difference in characteristics between textual images and medical images may cause eye strain and fatigue, such as when the reviewer shifts his or her attention from a bright textual image to a darker anatomical image. Accordingly, to solve these and other problems, embodiments described herein determine a classification for each medical image included in an exam and display each medical image based on the classification associated with each medical image.

Figure 2:
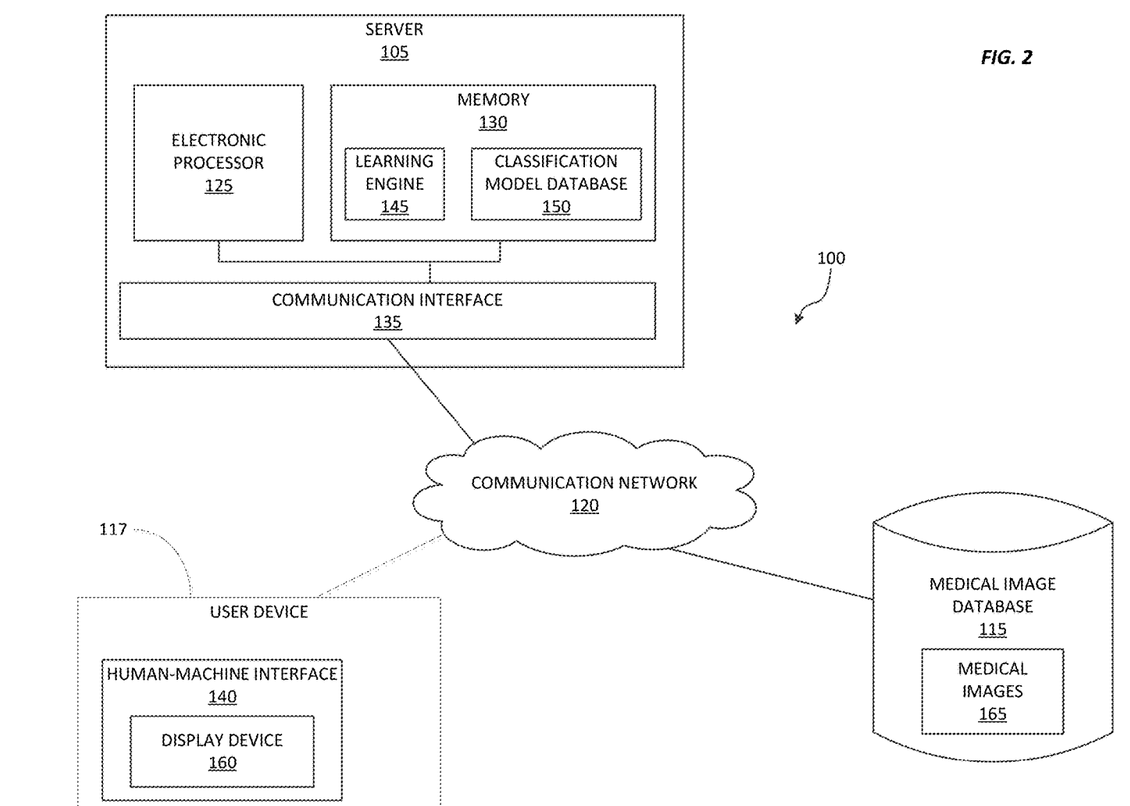
FIG. 2 schematically illustrates a system for displaying a medical image according to some embodiments.

FIG. 2 schematically illustrates a system 100 for displaying an image (for example, a medical image) according to some embodiments. The system 100 includes a server 105, a medical image database 115, and a user device 117. In some embodiments, the system 100 includes fewer, additional, or different components than illustrated in FIG. 2. For example, the system 100 may include multiple servers 105, medical image databases 115, user devices 117, or a combination thereof.

The server 105, the medical image database 115, and the user device 117 communicate over one or more wired or wireless communication networks 120. Portions of the communication network 120 may be implemented using a wide area network, such as the Internet, a local area network, such as a Bluetooth™ network or Wi-Fi, and combinations or derivatives thereof. Alternatively or in addition, in some embodiments, components of the system 100 communicate directly as compared to through the communication network 120. Also, in some embodiments, the components of the system 100 communicate through one or more intermediary devices not illustrated in FIG. 2.

The server 105 is a computing device, which may server as a gateway for the medical image database 115. For example, in some embodiments, the server 105 may be a PACS server. Alternatively, in some embodiments, the server 105 may be a server that communicates with a PACS server to access the medical image database 115. As illustrated in FIG. 2, the server 105 105 includes an electronic processor 125, a memory 130, and a communication interface 135. The electronic processor 125, the memory 130, and the communication interface 135 communicate wirelessly, over one or more communication lines or buses, or a combination thereof. The server 105 may include additional components than those illustrated in FIG. 2 in various configurations. The server 105 may also perform additional functionality other than the functionality described herein. Also, the functionality described herein as being performed by the server 105 may be distributed among multiple devices, such as multiple servers included in a cloud service environment. In addition, in some embodiments, the user device 117 may be configured to perform all or a portion of the functionality described herein as being performed by the server 105.

The electronic processor 125 includes a microprocessor, an application-specific integrated circuit (ASIC), or another suitable electronic device for processing data. The memory 130 includes a non-transitory computer-readable medium, such as read-only memory ("ROM"), random access memory ("RAM") (for example, dynamic RAM ("DRAM"), synchronous DRAM ("SDRAM"), and the like), electrically erasable programmable read-only memory ("EEPROM"), flash memory, a hard disk, a secure digital ("SD") card, another suitable memory device, or a combination thereof. The electronic processor 125 is configured to access and execute computer-readable instructions ("software") stored in the memory 130. The software may include firmware, one or more applications, program data, filters, rules, one or more program modules, and other executable instructions. For example, the software may include instructions and associated data for performing a set of functions, including the methods described herein.

For example, as illustrated in FIG. 2, the memory 130 may store a learning engine 145 and a classification model database 150. In some embodiments, the learning engine 145 develops a classification model using one or more machine learning functions. Machine learning functions are generally functions that allow a computer application to learn without being explicitly programmed. In particular, a computer application performing machine learning functions (sometimes referred to as a learning engine) is configured to develop an algorithm based on training data. For example, to perform supervised learning, the training data includes example inputs and corresponding desired (for example, actual) outputs, and the learning engine progressively develops a model (for example, a classification model) that maps inputs to the outputs included in the training data. Machine learning may be performed using various types of methods and mechanisms including but not limited to decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using all of these approaches, a computer program may ingest, parse, and understand data and progressively refine models for data analytics, including image analytics.

Accordingly, the learning engine 145 (as executed by the electronic processor 125) may perform machine learning using training data to develop a classification model that maps medical images 165 to one or more classifications. The training data may include, for example, medical images and their associated classifications. For example, the learning engine 145 may identify one or more unique characteristics of a medical image (for example, objects within the medical image, metadata associated with the medical image, and the like) and develop a classification model that maps the one or more unique characteristics to a particular classification. Accordingly, when a subsequent medical image is received, the electronic processor 125 may determine a classification for that subsequent medical image using the classification model developed by the learning engine 145. In other words, the electronic processor 125 determines a classification for each of the medical images 165 using a classification model that analyzes content of each of the medical images 165. Similarly, as described in more detail below, in some embodiments, the electronic processor 125 may use a classification model to determine what images should (and should not) be displayed to a particular user, such as based on a user's role, permissions, and the like. In some embodiments, the classification model may also specify display or presentation parameters for the medical images, such as hanging protocol, an filtering or modifications (for example, greyscale matching within a sequence of images), and the like.

Classification models generated by the learning engine 145 may be stored in the classification model database 150. As illustrated in FIG. 2, the classification model database 150 is included in the memory 130 of the server 105. It should be understood that, in some embodiments, the classification model database 150 is included in a separate device accessible by the server 105 (included in the server 105 or external to the server 105).

The communication interface 135 allows the server 105 to communicate with devices external to the server 105. For example, as illustrated in FIG. 2, the server 105 may communicate with the medical image database 115 through the communication interface 135. In particular, the communication interface 135 may include a port for receiving a wired connection to an external device (for example, a universal serial bus ("USB") cable and the like), a transceiver for establishing a wireless connection to an external device (for example, over one or more communication networks 120, such as the Internet, local area network ("LAN"), a wide area network ("WAN"), and the like), or a combination thereof.

The user device 117 is also a computing device and may include a desktop computer, a terminal, a workstation, a laptop computer, a tablet computer, a smart watch or other wearable, a smart television or whiteboard, or the like. Although not illustrated, the user device 117 may include similar components as the server 105 (an electronic processor, a memory, and a communication interface). The user device 117 may also include a human-machine interface 140 for interacting with a user. The human-machine interface 140 may include one or more input devices, one or more output devices, or a combination thereof. Accordingly, in some embodiments, the human-machine interface 140 allows a user to interact with (for example, provide input to and receive output from) the user device 117. For example, the human-machine interface 140 may include a keyboard, a cursor-control device (for example, a mouse), a touch screen, a scroll ball, a mechanical button, a display device (for example, a liquid crystal display ("LCD")), a printer, a speaker, a microphone, or a combination thereof. As illustrated in FIG. 2, in some embodiments, the human-machine interface 140 includes a display device 160. The display device 160 may be included in the same housing as the user device 117 or may communicate with the user device 117 over one or more wired or wireless connections. For example, in some embodiments, the display device 160 is a touchscreen included in a laptop computer or a tablet computer. In other embodiments, the display device 160 is a monitor, a television, or a projector coupled to a terminal, desktop computer, or the like via one or more cables.

The medical image database 115 stores a plurality of medical images 165. In some embodiments, the medical image database 115 is combined with the server 105. Alternatively or in addition, the medical images 165 may be stored within a plurality of databases, such as within a cloud service. Although not illustrated in FIG. 2, the medical image database 115 may include components similar to the server 105, such as an electronic processor, a memory, a communication interface and the like. For example, the medical image database 115 may include a communication interface configured to communicate (for example, receive data and transmit data) over the communication network 120.

As mentioned above, the medical images 165 stored in the medical image database 115 may include a variety of classifications or types. For example, the medical images 165 may include anatomical images, such as a lateral chest radiograph, a PA chest radiograph, and the like. Alternatively or in addition, the medical images 165 may include textual images, such as a referral form, a technologist worksheet, a medical record request form, a billing form, a screening form, another type of administrative form, and the like. For example, a medical professional may capture a picture of a billing form by scanning the billing form. The scanned version of the billing form may be stored in the medical image database 115 as a medical image 165. Accordingly, in some embodiments, a memory of the medical image database 115 stores the medical images 165 and associated data (for example, reports, metadata, and the like). For example, the medical image database 115 may include a picture archiving and communication system ("PACS"), a radiology information system ("RIS"), an electronic medical record ("EMR"), a hospital information system ("HIS"), an image study ordering system, and the like.

A user may use the user device 117 to access and view the medical images 165 and interact with the medical images 165. For example, the user may access the medical images 165 from the medical image database 115 (through a browser application or a dedicated application stored on the user device 117 that communicates with the server 105) and view the medical images 165 on the display device 160 associated with the user device 117. As noted above, the variety of image classifications included in an exam may interfere with the application of hanging protocols (for example, a set of rules), and ultimately, with the display of the exam to a reviewer. To solve this and other problems, the system 100 is configured to automatically determine a classification of one or more medical images 165 (for example, a first medical image, a second medical image, and the like). Based on the classification of the medical images 165, the methods and systems described herein display the medical images 165 to user (for example, a reviewer).

Figure 3:
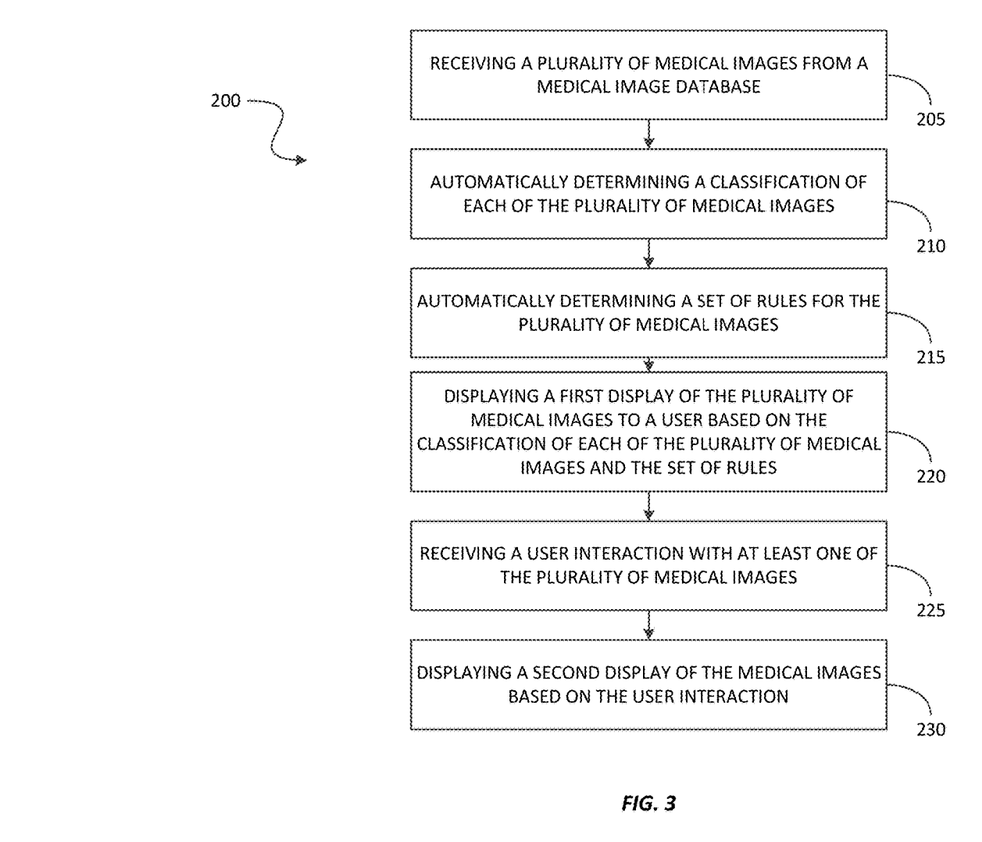
FIG. 3 is a flowchart illustrating a method for displaying a medical image using the system of FIG. 2 according to some embodiments.

For example, FIG. 3 is a flowchart illustrating a method 200 for displaying an image (for example, a medical image 165) according to some embodiments. The method 200 is described here as being performed by the server 105 (the electronic processor 125 executing instructions). However, as noted above, the functionality performed by the server 105 (or a portion thereof) may be performed by other devices, including, for example, the user device 117 (via an electronic processor executing instructions). As illustrated in FIG. 3, the method 200 includes receiving, with the electronic processor 125, one or more medical images 165 from the medical image database 115 (at block 205). In some embodiments, the electronic processor 125 receives the medical images 165 via the communication interface 135 from the medical image database 115 over the communication network 120. As noted above, in some embodiments, one or more medical images 165 may be stored at additional or different databases, servers, devices, or a combination thereof. Accordingly, in some embodiments, the electronic processor 125 receives the medical images 165 from additional or different databases, servers, devices, or a combination thereof. The image received by the server 105 may be based on a request for a particular medical exam received from the user device 117. In some embodiments, the request from the medical exam also includes information regarding a user making the request. However, in other embodiments, the classification process performed by the server 105 as described above may be performed in response to other triggering events, including, for example, the generation and storage of a new medical exam in the medical image database 115.

After receiving the medical images 165 from the medical image database 115 (at block 205), the electronic processor 125 automatically determines a classification of each of the medical images 165 (at block 210). As noted above, a classification of a medical image 165 may include, for example, an anatomical image or a textual image. Accordingly, the electronic processor 125 may determine that a first medical image is an anatomical image while a second medical image is a textual image and vice versa. In some embodiments, the electronic processor 125 is further configured to determine a subcategory for a medical image. For example, in some embodiments, when the electronic processor 125 determines that the medical image 165 is a textual image, the electronic processor 125 further determines a subcategory for the medical image 165. The subcategory may include, for example, a referral form, a technologist worksheet, a medical record, a request form, a billing form, a screening form, another administrative or textual form, or a combination thereof. In some embodiments, the electronic processor 125 displays the medical images 165 as described below based on the classification and the subcategory of the medical images 165 determined to be textual images.

In some embodiments, the electronic processor 125 determines the classification (and optionally subcategory) of each of the medical images 165 using one or more classification models stored in the classification model database 150. The electronic processor 125 may access the classification models stored in the classification model database 150 to determine a classification of each of the medical images 165. For example, in some embodiments, the server 105 identifies one or more unique characteristics of the medical image 165 and uses the one or more unique characteristics of the medical image 165 to select a classification model from the classification models stored in the classification model database 150. As noted above, the learning engine 145 may develop a plurality of classification models, wherein each classification model is associated with similar unique characteristics of medical images 165 (for example, an object within a medical image 165, metadata associated with the medical images 165, another unique characteristic of the medical image 165, or a combination thereof). Accordingly, the server 105 may use the identified unique characteristics of the medical image 165 to select a classification model associated with medical images most similar to the identified unique characteristics.

After selecting the appropriate classification model, the electronic processor 125 applies the selected classification model to the received medical images 165. As noted above, each classification model may take the medical image 165 (and, optionally, additional data) and output one or more classifications for each of the medical images 165. For example, in some embodiments, the electronic processor 125 applies the selected classification model to a received medical image 165 to determine a classification of the received medical image 165, such as an anatomical image or a textual image.

As illustrated in FIG. 3, optionally, the electronic processor 125 may also automatically determine a set of rules for the medical images 165 (at block 215). In some embodiments, the set of rules are rules related to the automated presentation of the medical images 165 based on a user's preferences. For example, the set of rules may be a "hanging protocol" feature of a PACS. In some embodiments, the set of rules are configurable. The set of rules may define, for example, a display preference, a software application preference, a display device preference, a viewing environment preference, an image arrangement preference, an image comparison preference, another preference, or a combination thereof.

In some embodiments, the electronic processor 125 determines the set of rules for the medical images 165 based on, for example, a user identification, a user role, a location of service, a patient demographic, a modality, an exam type, an exam group, another parameter, or a combination thereof. The set of rules may be stored in the memory 130 of the server 105, an external device, server, or database, and the like. In some embodiments, the electronic processor 125 receives (via the user device 117) a user selection of a set of rules for the medical images 165 (for example, with a request for a particular medical exam or separate from a request for an exam, such as part of configuring the system 100). Alternatively or in addition, the electronic processor 125 may use machine learning functions and techniques to develop the set of rules for the medical images 165, as similarly described above with respect to developing and applying the one or more classification models.

As illustrated in FIG. 3, the electronic processor 125 displays, via the display device 160 of the user device 117, a first display of the one or more medical images 165 to a user based on the classification of each of the medical images 165 (at block 220). In some embodiments, the first display of the medical images 165 also based on the set of rules as described above. In other words, how the electronic processor 125 displays the medical images 165 may be dependent on the classification of each of the medical images 165, the set of rules (for example, a hanging protocol) for the medical images 165, or a combination thereof. For example, the electronic processor 125 may display a screening form to a technologist requiring acknowledgment from the technologist (based on the set of rules for a user having the role of a technologist). As another example, the electronic processor 125 may display a referral form to a physician (based on the set of rules for a user having the role of a physician). As yet another example, the electronic processor 125 may display medical images 165 classified as textual images on a first display device (for example, the first display device 10) and medical images 165 classified as anatomical images on a second display device (for example, the second display device 15), as illustrated in FIG. 1. In this example, the electronic processor 125 displays the medical images 165 based on the classification of each medical image 165 as well as the set of rules (for example, textual images displayed on a first display device and anatomical images displayed on a second display device).

After displaying the first display of the medical images 165 to the user (at block 220), the electronic processor 125 may optionally receive a user interaction with the first display of the medical images 165 (at block 225). The user interaction may be with one or more of the medical images 165 included in the first display. The electronic processor 125 may receive the user interaction via the human-machine interface 140 of the user device 117. In some embodiments, the user interaction is a modification to a classification of one or more of the medical images 165, a modification to the set of rules for the medical images 165, or a combination thereof. For example, a user of the user device 117 viewing the first display of medical images 165 may identify an error in the classification of one of the medical images 165. Using the human-machine interface 140 of the user device 117, the user may interact with that medical image 165, the first display, or a combination thereof to correct the classification of that medical image 165. As another example, the user of the user device 117 viewing the first display of the medical images 165 may desire to alter a display preference (for example, a rule included in the set of rules) for viewing the first display. Using the human-machine interface 140, the user may interact with the medical image 165, the first display, or a combination thereof to modify the display preference (for example, a rule included in the set of rules).

When the user interaction is a modification to a classification of one or more of the medical images 165, the electronic processor 125 may optionally use the user interaction as feedback (for example, as training data for the learning engine 145). For example, the electronic processor 125 may provide the user interaction to the learning engine 145 to update or tune a previously generated classification model, develop a new classification model, or a combination thereof (for example, a modified classification model). When the user interaction is a modification to the set of rules for the medical images 165, the electronic processor 125 may use the user interaction to update one or more rules included in the set of rules. Accordingly, the user interaction may provide a closed feedback loop for the system 100.

After receiving a user interaction with (at block 225), the electronic processor 125 displays a second display of the medical images 165 (at block 230). In some embodiments, the second display of the medical images 165 is based on the user interaction received via the human-machine interface 140. Accordingly, the second display of the medical images 165 reflects any modifications or updates made by the electronic processor 125 in response to receiving the user interaction. The second display of the medical images 165 may be different from the first display. For example, the second display may be an updated version of the first display. Alternatively, in some embodiments, the second display of the medical images 165 is the same as the first display of the medical images 165.

In some embodiments, classifications may be stored with an image so that the image does not subsequently need to be classified. In some embodiments, the classification can be stored as part of metadata for the image. This metadata may be editable by a user, which allows a user to modify the automatic classification performed by the system. Also, in some embodiments, when metadata for an image is updated, the system 100 as described herein may be configured to re-assess any previous classifications to dynamically adjust to such metadata changes.

Thus, embodiments described herein apply one or more classification models (which may be generated using machine learning) to automatically distinguish anatomical images from other types of images, such as textual images, so that the anatomical can be displayed without interference. One or more rules may also be applied to determine the precise display, timing and presentation of images based on the classifications, such as who to display a particular image to, when, or in what sequence. Various features and advantages of the embodiments described herein are set forth in the following claims.

What is claimed is:

1. A system for displaying a medical image captured as part of a medical imaging procedure, the system comprising:
an electronic processor configured to receive a plurality of images from an image database, the plurality of images included in a medical exam associated with the procedure, automatically determine a classification for each of the plurality of images using a classification model analyzing content of each of the plurality of images, the classifications distinguishing images into either a category of textual images or a category of anatomical images, determine a set of rules displaying the plurality of images, and display a subset of the plurality of images based on the classification determined for each of the plurality of images and the set of rules.

2. The system of claim 1, wherein the electronic processor is configured to determine a subcategory for the image when the image is a textual image, wherein the subcategory includes at least one selected from a group consisting of a referral form, a technologist worksheet, a medical record, a request form, a billing form, and a screening form.

3. The system of claim 2, wherein the electronic processor is configured to display the image based on the subcategory for the image.

4. The system of claim 1, wherein the classification model is generated using machine learning.

5. The system of claim 1, wherein the electronic processor is further configured to receive a user interaction with the image.

6. The system of claim 5, wherein the electronic processor is further configured to update at least one rule included in the set of rules based on the user interaction.

7. The system of claim 5, wherein the electronic processor is further configured to update the classification model based on the user interaction.

8. The system of claim 1, wherein the set of rules defines at least one selected from a group consisting of a display preference, a software application preference, a display device preference, a viewing environment preference, an image arrangement preference, and an image comparison preference.

9. A method for displaying a plurality of medical images, the method comprising:

receiving, with an electronic processor, the plurality of medical images from a medical image database;

determining, with the electronic processor, a classification of each of the plurality of medical images using a classification model, wherein the classifications for each of the plurality of medical images distinguishes the images into either a category of textual images or a category of anatomical images;

determining, with the electronic processor, a set of rules for the plurality of medical images;

displaying, with the electronic processor, a first display of at least a subset of the plurality of medical images to a user via a display device based on the classification of each of the plurality of medical images and the set of rules;

receiving, with the electronic processor, a user interaction with at least one of the plurality of medical images; and displaying, with the electronic processor, a second display of the medical images based on the user interaction.

10. The method of claim 9, wherein determining the classification using the classification model includes determining the classification using a classification model developed using machine learning.

11. The method of claim 9, wherein determining the set of rules includes determining the set of rules based on at least one selected from a group consisting of a user identification, a user role, a location of service, a patient demographic, a modality, an exam type, and an exam group.

12. The method of claim 9, further comprising modifying at least one rule included in the set of rules based on the user interaction.

13. The method of claim 9, wherein receiving the user interaction includes receiving a modification to the classification of one or more of the plurality of medical images.

14. The method of claim 9, further comprising determining a subcategory of one or more of the plurality of medical images when one or more of the plurality of medical images are textual images.

15. The method of claim 9, wherein displaying the second display includes displaying the second display different from the first display.

16. A non-transitory, computer-readable medium storing instructions that, when executed by an electronic processor, perform a set of functions, the set of functions comprising:

receiving a first medical image from a medical image database in response to a request from a user for images included in a medical exam;

automatically determining a first classification of the first medical image using a classification model, the classification model classifying an image as a textual image or an anatomical image;

automatically determining whether to display the first medical image to a user based on the first classification;

receiving a second medical image from the medical image database in response to the request;

automatically determining a second classification of the second medical image using the classification model; and automatically determining whether to display the second medical image to the user based on the second classification.

17. The computer-readable medium of claim 16, wherein the set of functions further includes receiving a user interaction with the first medical image.

18. The computer-readable medium of claim 17, wherein receiving the user interface includes receiving a modification to the first classification and wherein the set of functions further includes automatically modifying the classification model based on the modification.

19. The computer-readable medium of claim 16, the set of functions further comprising:

determining a set of rules for the first medical image, the set of rules defining at least one selected from a group consisting of a user identification, a user role, a location of service, a patient demographic, a modality, an exam type, and an exam group.

20. The computer-readable medium of claim 19, wherein displaying the first medical image includes displaying the first medical image based on the set of rules.

* * * * *